United States Patent [19]

Failli et al.

[11] Patent Number: 5,260,299

[45] Date of Patent: Nov. 9, 1993

[54] RAPAMYCIN 42-SULFONATES AND 42-(N-CARBOALKOXY)SULFAMATES USEFUL AS IMMUNOSUPPRESSIVE AGENTS

[75] Inventors: Amedeo A. Failli, Princeton Junction, N.J.; Wenling Kao, Paoli; Robert J. Steffan, Langhorne, both of Pa.; Robert L. Vogel, Stratford, N.J.

[73] Assignee: American Home Products Corporation, New York, N.Y.

[21] Appl. No.: 917,555

[22] Filed: Jul. 21, 1992

Related U.S. Application Data

[62] Division of Ser. No. 846,637, Mar. 5, 1992, Pat. No. 5,177,203.

[51] Int. Cl.⁵ .......................... A61K 31/395
[52] U.S. Cl. ..................... 514/291; 540/456
[58] Field of Search ......................... 514/291

[56] References Cited

U.S. PATENT DOCUMENTS 5,177,203 1/1993 Failli et al. .......................... 540/456

Primary Examiner—Robert T. Bond
Attorney, Agent, or Firm—Walter Patton

[57] ABSTRACT

A derivative of rapamycin of general formula (I)

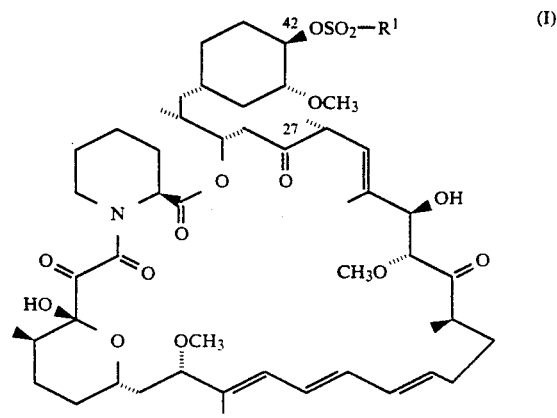

where $R^1$ is alkyl, alkenyl, or alkynyl containing 1 to 6 carbon atoms; or an aromatic moiety selected from the group consisting of phenyl and naphthyl or a heterocyclic moiety selected from the group consisting of thiophenyl and quinolinyl or $NHCO_2R^2$ wherein $R^2$ is lower alkyl containing 1 to 6 carbon atoms or a pharmaceutically acceptable salt thereof, which by virtue of its immunosuppressive activity is useful in treating transplantation rejection, host versus graft disease, autoimmune diseases, and diseases of inflammation.

1 Claim, No Drawings

RAPAMYCIN 42-SULFONATES AND 42-(N-CARBOALKOXY)SULFAMATES USEFUL AS IMMUNOSUPPRESSIVE AGENTS

This is a division of application Ser. No. 07/846,637 filed Mar. 5, 1992, now U.S. Pat. No. 5,177,203.

BACKGROUND OF THE INVENTION

This invention relates to rapamycin 42-sulfonates and 42-(N-carboalkoxy)sulfamates and a method for using them in the treatment of transplantation rejection, host versus graft disease, autoimmune diseases, diseases of inflammation, and fungal infections.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55,48 (1976)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Rapamycin therefore is also useful in preventing transplant rejection [FASEB 3, 3411 (1989); FASEB 3, 5256 (1989); and R. Y. Calne et al., Lancet 1183 (1978)].

Mono- and diacylated derivatives of rapamycin have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31-and 42-positions.

DESCRIPTION OF THE INVENTION

This invention relates to rapamycin 42-sulfonates and 42-(N-carboalkoxy)sulfamates of general formula (I)

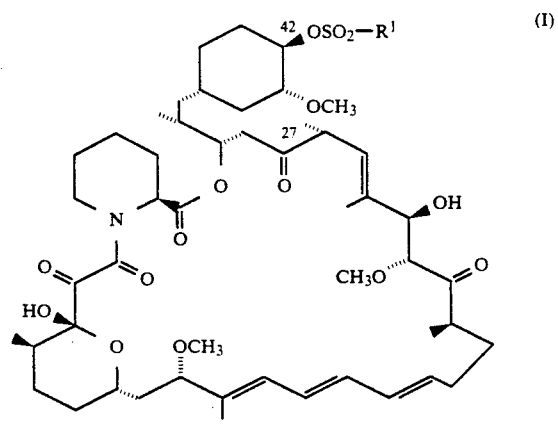

where $R^1$ is alkyl, alkenyl, or alkynyl containing 1 to 6 carbon atoms; or an aromatic moiety selected from the group consisting of phenyl and naphthyl or a heterocyclic moiety selected from the group consisting of thiophenyl and quinolinyl or $NHCO_2R^2$ wherein $R^2$ is lower alkyl containing 1 to 6 carbon atoms or a pharmaceutically acceptable salt thereof.

The rapamycin 42-sulfonates of this invention can be prepared by the standard literature procedure as outlined below.

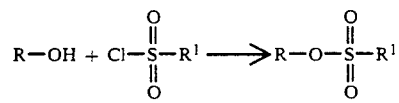

The sulfonate formation between alcohol and sufonyl halide has been described [Jerry March, Advanced Organic Chemistry, 3rd edition, published in 1985, page 444]. The specific reaction condition employed in this invention was developed by S. Rakhit of Ayerst Laboratories and reported in U.S. Pat. No. 4,316,855 (Feb. 23, 1982).

The 42-(N-carboalkoxy)sulfamates of the present invention can also be prepared by reaction of rapamycin with an alkyl(carboxysulfamoyl)triethylammonium hydroxide inner salt (Burgess Salts; see G. M. Atkins Jr. and E. M. Burgess, J. Am. Chem. Soc., 90, 4744, 1968; E. M. Burgess, H. R. Penton Jr. and E. A. Taylor, J. Org. Chem. 38, 26, 1978).

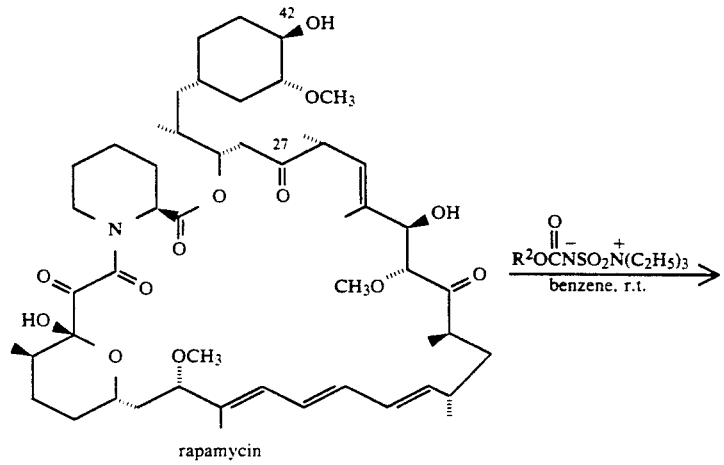

rapamycin

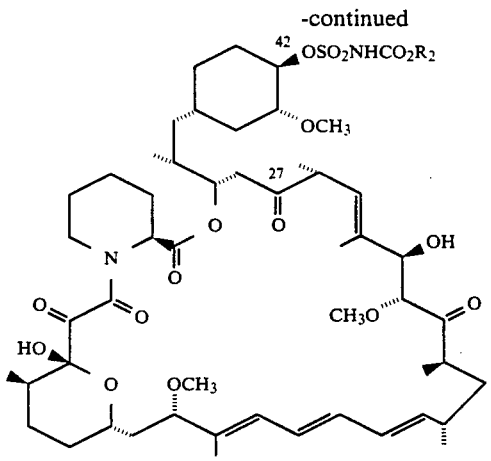

-continued wherein R² is as defined above.

The pharmaceutically acceptable salts may be formed from inorganic cations such as sodium, potassium, and the like.

The following examples illustrate the preparation of representative compounds of this invention.

EXAMPLE 1

Rapamycin 42-ester with 5-(dimethylamino)-1-naphthalenesulfonic acid

A solution of 200 mg (0.22 mmol) of rapamycin in 2 mL of pyridine was treated at 0° C. under anhydrous conditions with 840 mg (3.1 mmol) of dansyl chloride and stirred at room temperature for 24 hours. The reaction mixture was diluted at 0° C. with 30 mL of 2N HCl and extracted with ethyl acetate. The ethyl acetate extract was washed with brine, dried with MsSO₄ and evaporated. The residue was chromatographed on silica gel. Elution with 25% ethyl acetate in benzene afforded 150 mg of the title product as a light yellow powder, m.p. 101°-104° C.

IR: 3430 (OH), 1740 (sh), 1720 (both C=O), 1650 (amide C=O), 1450, 1355, 1170 (sulfonate), 1100, 985, 960 cm⁻¹.

¹H NMR (CDCl₃, 400 MHz) δ8.58 (d, 1H, H₁), 8.32 (d, 1H, H₃), 8.25 (m, 1H, H₂), 7.53 (m, 2H, H₅ and H₆), 7.19 (d, 1H, H₄), 3.31, 3.13, 2.72 (all s, 3H, —O—CH₃), 2.79(s, 6H, —N(CH₃)(CH₃)) ppm.

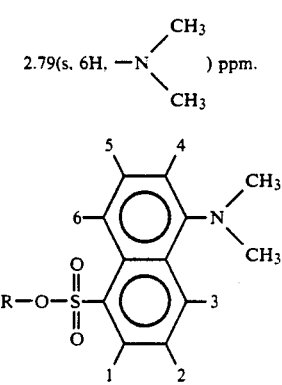

MS (neg. ion FAB) 1146 (M⁻), 912, 590, 250.

EXAMPLE 2

Rapamycin 42-ester with 4-methylbenzenesulfonic acid

A solution of 6.0 g (31.6 mmol) p-toluenesulfonyl chloride in 25 mL pyridine was added to a solution of 10.0 g (10.9 mmol) rapamycin at 0° C. and the resulting solution was stirred at 20° C. for 22 hours. Cold 2N HCl (240 mL) was added and the product was extracted into ethyl acetate, washed with brine, dried over MgSO₄ and evaporated to a yellow solid. Chromatography on silica gel eluted with 20% ethyl acetate in methylene chloride afforded 5.3 g product as a white solid, m.p. 108°-116° C.

IR(KBr): 3410, 2910, 1710, 1640, 1440, 1160 and 655 cm⁻¹.

NMR (CDCl₃, 400 MHz): δ7.80 (d, 2H, aromatic), 732 (d, 2H, aromatic), 3.33 (s, 3H), 3.14 (s, 3H), 3.13 (s, 3H), 2.44 (s, 3H).

MS (neg. ion FAB): 1067 (M⁻), 590, 171, 155.

EXAMPLE 3

Rapamycin 42-ester with 2-thiophenesulfonic acid

A solution of 0.18 g (0.2 mmol) rapamycin and 0.13 g (0.71 mmol) 2-thiophenesulfonyl chloride in 2 mL pyridine was heated at 55° C. for 4 hours, then cooled to 20° C. and treated with 40 mL 1N HCl. The product was extracted into ethyl acetate, washed with brine, dried over MgSO₄ and stripped of solvent. Chromatography on silica gel eluted with 20% ethyl acetate in methylene chloride afforded 40 mg title compound as a white solid, m.p. 114°-119° C.

IR (KBr): 3420, 2915, 1712, 1644, 1440, 1365, 1170 and 660 cm⁻¹.

NMR (CDCl₃, 400 MHz): δ7.67 (1H, aromatic), 7.62 (1H, aromatic), 7.07 (1H, aromatic), 3.29 (s, 3H, OCH₃), 3.14 (s, 3H, OCH₃), 3.09 (s, 3H, OCH₃).

MS (neg. ion FAB): 1059 (M⁻), 912, 590, 163.

EXAMPLE 4

Rapamycin 42-ester with 4-[[4-(dimethylamino)phenyl]aza]benzenesulfonic acid

Dabsyl chloride (0.83 g, 2.57 mmol) was added to a solution of 0.54 g (0.59 mmol) rapamycin in 30 mL dry pyridine and the solution heated at 65°-70° C. for 24 hours. Upon cooling, the reaction mixture was partitioned between 200 mL 2N HCl and 50 mL ethyl acetate. The product was dried over MgSO₄, stripped of solvent and chromatographed on silica gel eluted with 30% ethyl acetate in methylene chloride, to afford the title compound as a bright red solid, m.p. 118°-133°

IR (KBr): 3430, 2930, 1720, 1600, 1360, 1142, 683 and 602 cm$^{-1}$.

NMR (CDCl$_3$, 400 MHz): δ8.00 (2H, aromatic), 7.93 (4H, aromatic), 6.76 (2H, aromatic), 3.33 (s, 3H, OCH$_3$), 3.135 (s, 3H, OCH$_3$), 3.126 (s, 3H, OCH$_3$).

MS (pos. FAB): 1223 (MNa$^+$), 1169, 1137, 918, 306.

EXAMPLE 5

Rapamycin 42-ester with 1-naphthalene sulfonic acid

1-Naphthalenesulfonyl chloride (0.48 g, 0.2.1 mmol) was added to a solution of (0.54 g, 0.59 mmol) rapamycin in 11 mlL pyridine and the resulting solution was stirred at 20° C. for 44 hours. Cold 2N HCl (75 mL) was added and the product was extracted into ethyl acetate, washed with brine, dried over MgSO$_4$ and evaporated to a tan solid. Chromatography on slica gel eluted with 20% ethyl acetate in methylene chloride yielded 30 mg product as a white solid, m.p. 110°-131° C.

IR (KBr): 3440, 2925, 1720, 1645, 1450, 1175 and 765 cm$^{-1}$.

NMR (CDCl$_3$, 400 MHz): δ8.65 (1H), 8.26 (1H), 8.10 (2H), 7.93 (1H), 7.70 (1H), 7.62-7.53 (complex, 2H), 3.32 (s, 3H, OCH$_3$), 3.13 (s, 3H, OCH$_3$), 2.64 (s, 3H, OCH$_3$).

MS (neg. FAB): 1103 (M$^-$), 912, 590.

EXAMPLE 6

Rapamycin 42-ester with 8-quinolinesulfonic acid

A solution of (0.30 g, 0.33 mmol) rapamycin and (0.29 g, 1.28 mmol) 8-quinolinesulfonyl chloride in 5 mL pyridine was stirred at 20° C. for 24 hours. The reaction mixture was partitioned between 2N HCl (10 mL) and ethyl acetate.

The organic layer was washed with brine, dried over MgSO$_4$, stripped of solvent and chromatographed on silica gel eluted with 30% ethyl acetate in methylene chloride, affording 130 mg of title compound as a white solid, mp 120°-165° C.

IR (KBr): 3430, 2925, 1715, 1640, 1170, 985 and 785 cm$^{-1}$.

NMR (CDCl$_3$, 400 MHz): δ9.18 (1H), 8.49 (1H), 8.25 (1H), 8.09 (1H), 7.65 (1H), 7.55 (1H), 3.32 (s, 3H, OCH$_3$), 3.13 (s, 3H, OCH$_3$), 2.60 (s, 3H, OCH$_3$).

MS (neg. FAB): 1104 (M$^-$), 912, 590, 208.

EXAMPLE 7

Rapamycin 42-methanesulfonate, hemiethylacetate, hemihydrate

Under an atmosphere of nitrogen, an ice cold solution of rapamycin (0.46 g, 0.5 mmol) and triethyl amine (0.14 mL, 1.0 mmol) in 5 mL of dry CH$_2$Cl$_2$ was treated dropwise with methanesulfonyl chloride (0.943 mL, 0.55 mmol). The ice bath was removed and the solution stirred at ambient temperature for one hour. The reaction mixture was diluted with CH$_2$Cl$_2$ and washed successively with H$_2$O and brine. After drying (Na$_2$SO$_4$), the solvent was removed in vacuo to give a yellow foam. Purification by flash chromatography (silica Merck 60, ethyl acetate-hexane 1:1) afforded the title compound (0.37 g, 75% white solid).

NMR (400 MHz, CDCl$_3$): δ1.65 (3H, CH$_3$C=C), 1.74+1.75 (2s, 3H, CH$_3$C=C), 3.06 (s, 3H, CH$_3$SO$_2$), 3.13 (s, 3H, OCH$_3$), 3.34 (s, 3H, OCH$_3$), 3.4003 (s, 3H, OCH$_3$).

MS (neg. ion FAB, m/z): 991 (M)$^-$, 590, 399.

Anal. cal'd for C$_{52}$H$_{81}$NO$_{15}$S+0.5 H$_2$O+0.5 C$_4$H$_8$O$_2$: C, 62.05; H, 8.29; N, 1.34. Found: C, 61.63; H, 8.34; N, 1.49.

EXAMPLE 8

Rapamycin 42-(2,2,2-trifluoroethane sulfonate), dihydrate

Under an atmosphere of nitrogen, a solution of rapamycin (0.46 g, 0.5 mmol) and triethylamine (0.15 mL, 1.1 mmol) in 2 mL of dry CH$_2$Cl$_2$ was treated in one portion with 2,2,2-trifluoroethane sulfonyl chloride (0.06 mL, 0.55 mmol). The solution was stirred overnight at ambient temperature. The solvent was evaporated in vacuo to give a yellow foam. The crude product mixture was purified by MPLC (silica Lichrosorb 60, Merck 440*37 mm, ethyl acetate-hexane 1:2, flowrate 20 mL/min) to give the title compound.

NMR (400 MHz, CDCl$_3$): δ1.65 (s, 3H, CH$_3$C=C), 1.749+1.752 (2s, 3H, CH$_3$C=C), 3.14 (s, 3H, OCH$_3$), 3.34 (s, 3H, OCH$_3$), 3.37 (s, 3H, OCH$_3$).

MS (neg. ion FAB, m/z): 1059 (M)$^-$, 590, 560, 427, 163.

Anal. cal'd for C$_{52}$H$_{81}$NO$_{15}$S+2 H$_2$O: C, 58.02; H, 7.72; N, 1.28. Found: C, 57.94; H, 7.96; N, 1.22.

EXAMPLE 9

42-O-[[(Methoxycarbonyl)]amino]sulfonyl]rapamycin

Under anhydrous conditions, a solution of rapamycin (0.5 g, 0.55 mmol) and methyl(carboxysulfamoyl)triethylammonium inner salt (0.25 g, 1.2 mmol, prepared as described by Burgess et al., J. Org. Chem. 38, 26, 1978) in 5 mL of benzene was stirred at ambient temperature overnight. The reaction mixture was then diluted with EtOAc (50 mL) and the solution was washed with water and brine and dried (Na$_2$SO$_4$). Removal of the solvent in vacuo yielded an off-white solid which was further purified by MPLC (silica Merck 60 Lichroprep, 440*37 mm, ethyl acetate-hexane 2:1→methanol) to provide the title product as a yellow solid (0.247 g, 43%).

$^1$H NMR (CDCl$_3$, 400 MHz): δ1.65 (s, 3H, CH$_3$C=C), 1.78 (s, 3H, CH$_3$C=C), 3.13 (m, 3H, CH$_3$O), 3.39 (m, 6H, CH$_3$O), 3.71 (s, 3H, CO$_2$CH$_3$).

MS (neg. ion FAB, m/z): 1050 (M—H)—.

The comitogen-induced thymocyte proliferation procedure (LAF) was used as an in vitro measure of the immunosuppressive effects of representative compounds. Briefly, cells from the thymus of normal BALB/c mice were cultured for 72 hours with PHA and IL-1 and pulsed with tritiated thymidine during the last six hours. Cells are cultured with and without various concentrations of rapamycin, cyclosporin A, or test compound. Cells are harvested and incorporated; radioactivity is determined. Inhibition of lymphoproliferation is assessed in precent change in counts per minute from non-drug treated controls. The results are expressed by the following ratio:

$^3$H-control thymus cells — H$^3$-rapamycin-treated thymus cells
$^3$H-control thymus cells — H$^3$-test compound-treated cells A mixed lymphocyte reaction (MLR) occurs when lymphoid cells from genetically distinct animals are combined in tissue culture. Each stimulates the other to undergo blast transformation which results in increased DNA synthesis that can be quantified by the incorporation of tritiated thymidine. Since stimulating a MLR is a function of disparity at Major Histocompatibility antigens, an in vivo popliteal lymph node (PLN) test procedure closely correlates to host vs. graft disease. Briefly, irradiated spleen cells from BALB/c donors are injected into the right hind foot pad of recipient $C_3H$ mice. The drug is given daily, p.o. from Day 0 to Day 4. On Day 3 and Day 4, tritiated thymidine is given i.p., b.i.d. On Day 5, the hind popliteal lymph nodes are removed and dissolved, and radioactivity counted. The corresponding left PLN serves as the control for the PLN from the injected hind foot. Percent suppression is calculated using the non-drug treated animals as allogenic control. Rapamycin at a dose of 6 mg/kg, p.o. gave 86% suppression, whereas cyclosporin A at the same dose gave 43% suppression. Results are expressed by the following ratio:

$$\frac{\frac{^3\text{H-PLN cells control C3H mouse}}{^3\text{H-PLN cells control C3H mouse}} - \frac{^3\text{H-PLN cells rapamycin-treated C3H mouse}}{^3\text{H-PLN cells test compound-treated C3H mouse}}}$$

The second in vivo test procedure is designed to determine the survival time of pinch skin graft from male DBA/2 donors transplanted to male BALB/c recipients. The method is adapted from Billingham R. E. and Medawar P. B., J. Exp. Biol. 28:385-402 (1951). Briefly, a pinch skin graft from the donor is grafted on the dorsum of the recipient as a homograft, and an autograft is used as control in the same region. The recipients are treated with either varying concentrations of cyclosporin A as test control or the test compound, intraperitoneally. Untreated recipients serve as rejection control. The graft is monitored daily and observations are recorded until the graft becomes dry and forms a blackened scab. This is considered as the rejection day. The mean graft survival time (number of days±S.D.) of the drug treatment group is compared with the control group.

BIOLOGICAL DATA

The following table summarizes the results of representative compounds of this invention in these three standard test procedures.

TABLE 1

| | Biological Activity | | |
|---|---|---|---|
| Example | LAF Assay (R/A ratio) | PLN (R/A ratio) | Skin Graft Model (days + SD) |
| 1 | 0.26 | — | 8.0 ± 0.9 |
| 2 | 0.21 | — | 8.7 ± 1.2 |
| 3 | 0.23 | 1.23 (i.p.) | 9.3 ± 0.8 |
| 4 | 0.03 | — | — |
| 5 | 0.19 | 0.92 (i.p.) | 9.5 ± 0.3 |
| 6 | 1.32 | 0.08 (i.p.) | 10.7 ± 2.1 |
| 7 | 1.70 | 0.36 (i.p.) | 9.83 ± 0.98 |
| 8 | 0.85 | 0.83 (i.p.) | 10.0 ± 1.4 |
| 9 | 0.01 | 0.93 (i.p.) | 10.33 ± 0.24 |

The results of these standard pharmacological test procedures demonstrate high immunosuppressive activity both in vitro and in vivo for the compounds of the present invention. A positive ratio in the LAF and PLN test procedures indicates suppression of T-cell proliferation. As transplanted pinch skin grafts are typically rejected within 6-7 days without the use of an immunosuppressive agent, the substantial increase in survival time of the skin grant when treated with the compounds of the present invention further demonstrate their utility as immunosuppressive agents.

Based on the results of these standard pharmacological test procedures, the compounds of this invention are useful in the prevention and treatment of transplant rejection such as heart, kidney, liver, bone marrow, and skin transplants; graft versus host disease; autoimmune and proliferative diseases such as, systemic lupus erythematosus, rheumatoid arthritis, type 1 diabetes, multiple sclerosis, glomerular nephritis, Hashimoto's thyroiditis, myasthenia gravis, uveitis and psoriasis; diseases of inflammation such as dermatitis, eczema, seborrhea and inflammatory bowel disease; and fungal infections.

The compounds may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular intraperitoneal or subcutaneous injection. Sterile solutions can also be administered intravenously. The compound can also be administered orally either in liquid or solid compositions form.

Preferably, the pharmaceutical composition is in unit dosage form, e.g., as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

What is claimed is:

1. A method of treating transplantation rejection, host versus graft disease, autoimmune diseases, and diseases of inflammation in a mammal by administering an effective amount of a compound of formula (I)

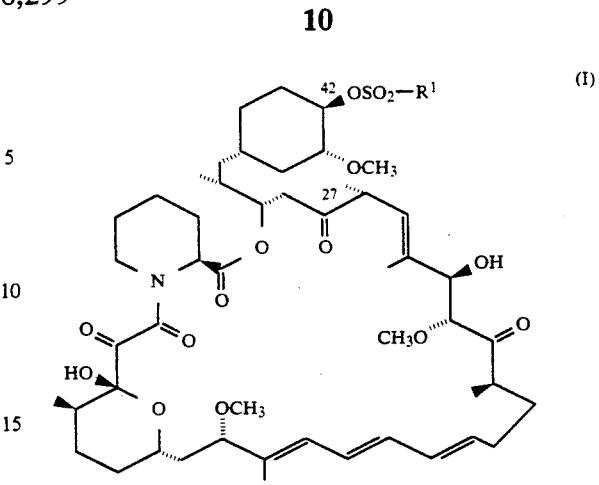

where $R^1$ is alkyl, alkenyl, or alkynyl containing 1 to 6 carbon atoms; or an aromatic moiety selected from the group consisting of phenyl and naphthyl or a heterocyclic moiety selected from the group consisting of thiophenyl and quinolinyl or $NHCO_2R^2$ wherein $R^2$ is lower alkyl containing 1 to 6 carbon atoms or a pharmaceutically acceptable salt thereof.

* * * * *